US011884743B2

(12) United States Patent
Guo et al.

(10) Patent No.: US 11,884,743 B2
(45) Date of Patent: Jan. 30, 2024

(54) PREPARATION AND APPLICATION OF AN INTACT RECOMBINANT ANTIBODY SPECIFIC TO CLOTHIANIDIN BASED ON THE IDENTIFIED VARIABLE REGION SEQUENCE

(71) Applicant: Zhejiang University, Zhejiang (CN)

(72) Inventors: Yirong Guo, Zhejiang (CN); Yunyun Chang, Zhejiang (CN); Rubing Zou, Zhejiang (CN); Ying Zhao, Zhejiang (CN); Shasha Jiao, Zhejiang (CN); Guonian Zhu, Zhejiang (CN)

(73) Assignee: Zhejiang University, Zhejiang (CN)

( * ) Notice: Subject to any disclaimer, the term of this patent is extended or adjusted under 35 U.S.C. 154(b) by 0 days.

(21) Appl. No.: 17/921,355

(22) PCT Filed: Oct. 16, 2020

(86) PCT No.: PCT/CN2020/121649
§ 371 (c)(1),
(2) Date: Oct. 26, 2022

(87) PCT Pub. No.: WO2021/218053
PCT Pub. Date: Nov. 4, 2021

(65) Prior Publication Data
US 2023/0174676 A1  Jun. 8, 2023

(30) Foreign Application Priority Data

Apr. 26, 2020 (CN) .......................... 202010336548.9

(51) Int. Cl.
*C07K 16/44* (2006.01)
*G01N 33/543* (2006.01)

(52) U.S. Cl.
CPC ....... *C07K 16/44* (2013.01); *G01N 33/54387* (2021.08); *C07K 2317/56* (2013.01); *C07K 2317/64* (2013.01); *G01N 2430/10* (2013.01)

(58) Field of Classification Search
None
See application file for complete search history.

(56) References Cited

FOREIGN PATENT DOCUMENTS

| CN | 102875671 | 1/2013 |
| CN | 105400742 | 3/2016 |
| CN | 108948188 | 12/2018 |

OTHER PUBLICATIONS

Rudikoff et al. 'Single amino acid substitutions altering antigen binding specificity.' PNAS 79:1979-1983, 1982.*
Colman et al. 'Effects of amino acid sequence changes on antibody-antigen interactions.' Res Immunol. 145(1):33-6, 1994.*
D'Angelo et al., Many Routes to an Antibody Heavy-Chain CDR3: Necessary, Yet Insufficient, for Specific Binding, Frontiers in Immunology vol. 9, Article 395 Mar. 2018; doi:10.3389/fimmu.2018.00395.*
Piche-Nicholas et al., Changes in complemetarity-determining regions significantly alter IgG binding to the neonatal Fc receptor (FcRN) and pharmacokinetics, MABS 2018, vol. 10, No. 1, 81-94, doi.org/10.1080/19420862.2017.1389355.*
Ming Li et al., "Development of Immunoassays for Detecting Clothianidin Residue in Agricultural Products", Journal of Agricultural and Food Chemistry, Mar. 2013, pp. 3619-3623.
Ming Li et al., "Detecting clothianidin residues in environmental and agricultural samples using rapid, sensitive enzyme-linked immunosorbent assay and gold immunochromatographic assay", Science of the Total Environment, Aug. 2014, pp. 1-6.
Mikiko Uchigashima et al., "Development of Immunoassay Based on Monoclonal Antibody Reacted with the Neonicotinoid Insecticides Clothianidin and Dinotefuran", Sensors, Nov. 2012, pp. 15858-15872.
"International Search Report (Form PCT/ISA/210) of PCT/CN2020/121649," dated Jan. 27, 2021, with English translation thereof, pp. 1-6.
"Written Opinion of the International Searching Authority (Form PCT/ISA/237) of PCT/ CN2020/121649," dated Nov. 10, 2021, with English translation thereof, pp. 1-9.

* cited by examiner

Primary Examiner — Nora M Rooney
(74) Attorney, Agent, or Firm — JCIPRNET

(57) ABSTRACT

A variable region sequence of a specific antibody against clothianidin is provided. A gene encoding a heavy chain variable region of the antibody has an amino acid sequence shown in SEQ ID NO: 2. An intact recombinant antibody against clothianidin is provided. The intact recombinant antibody includes a heavy chain constant region, a heavy chain variable region, a light chain constant region and a light chain variable region, wherein a gene encoding the heavy chain variable region has an amino acid sequence shown in SEQ ID NO: 2. An immunostrip containing the antibody for rapid detection of clothianidin residue is also provided. The sequence genes obtained are linked to an expression vector containing a heavy chain constant region gene and a light chain constant region gene, respectively, and an intact recombinant antibody is expressed and obtained by using mammalian cells with a double-plasmid system.

7 Claims, 2 Drawing Sheets

Specification includes a Sequence Listing.

PREPARATION AND APPLICATION OF AN INTACT RECOMBINANT ANTIBODY SPECIFIC TO CLOTHIANIDIN BASED ON THE IDENTIFIED VARIABLE REGION SEQUENCE

CROSS-REFERENCE TO RELATED APPLICATION

This is a 371 application of the International PCT application serial no. PCT/CN2020/121649, filed on Oct. 16, 2020, which claims the priority benefits of China Application No. 202010336548.9, filed on Apr. 26, 2020. The entirety of each of the above-mentioned patent applications is hereby incorporated by reference herein and made a part of this specification.

REFERENCE TO A SEQUENCE LISTING

The instant application contains a Sequencing Listing which has been submitted electronically in ASCII file and is hereby incorporated by reference in its entirety. Said ASCII copy, created on Jun. 13, 2023, is named 128121-US-sequencing list and is 4,327 bytes in size.

TECHNICAL FIELD

The present disclosure belongs to the technical field of genetic engineering, and particularly relates to the use of variable region sequence for preparing an intact recombinant antibody specific to clothianidin.

DESCRIPTION OF RELATED ART

Clothianidin is a new type of nicotinic insecticide with thiazole ring. Because of its unique structure and superior performance to traditional nicotinic insecticides, it is widely used to control the harm of various pests to crops. Clothianidin has excellent internal absorption and penetration, so it will be distributed in various parts of the crop. Because of its strong water solubility and long half-life, it can easily to enter surface water and soil through rainfall and irrigation. Studies have shown that there are high levels of clothianidin residues in surface water, sediments and soils, which pose a great threat to ecological health, non-target pollinators and aquatic invertebrates. The EU has banned the use of clothianidin in outdoor environment, and the maximum residue limits (MRLs) for clothianidin in different food products are 0.01-1.5 mg/mg in EU standard. In China, the MRLs of clothianidin are set at 0.01-2 mg/kg. In order to prevent consumers and beneficial organisms from the hazards of clothianidin residue, the monitoring of clothianidin in environment and agricultural products is of great significance.

At present, the detection methods for clothianidin mainly include instrumental analytical methods and immunoassays. Instrumental analytical methods such as HPLC, GC and MS have high precision, accuracy and sensitivity, and can meet the requirements of accurate qualitative and quantitative detection of clothianidin. However, instrumental analysis methods require expensive analytical instruments, professional experimental personnel and complex sample pretreatment methods, so it is difficult to achieve large-scale rapid on-site analysis. The rapid detection method of immunoassay can meet the needs of on-site detection of pesticide residues and large-scale sample screening.

Although there have been reports of monoclonal antibodies against clothianidin, these antibodies have cross-reactivity with dinotefuran. Li Ming et al. reported the preparation and application of anti-clothianidin monoclonal antibody with an antibody sensitivity (inhibition medium concentration $IC_{50}$) of 26.6 ng/mL, and the cross-reaction rate with dinotefuran was 47.8% (Detecting clothianidin residues in environmental and agricultural samples using rapid, sensitive enzyme-linked immunosorbent assay and gold immunochromatographic assay. SCI TOTAL ENVIRON 2014, 499: 1-6). The $IC_{50}$ of anti-clothianidin antibody reported by Uchigashima et al. was 4.4 ng/mL, and the cross-reaction rate with dinotefuran was 64% (Development of Immunoassay Based on Monoclonal Antibody Reacted with the Neonicotinoid Insecticides Clothianidin and Dinotefuran. SENSORS-BASEL 2012, 12(11): 15858-15872).

Dinotefuran is a new kind of neonicotinoid pesticide with a very different chemical structure from the common neonicotinoid pesticides. Because it has a wide insecticidal spectrum and is safe to crops, humans, animals and the environment, the usage of dinotefuran in practical agricultural production is not less than clothianidin, and its physicochemical properties are similar to other neonicotinoid pesticides. Thus, dinotefuran residue is often found in the environment. In the practical on-site detection work, it is hard to distinguish clothianidin and dinotefuran rapidly, when the anti-clothianidin monoclonal antibody that can cross-recognize dinotefuran is used for the immunoassay. Therefore, it is in urgent need to develop a highly specific and highly sensitive anti-clothianidin antibody.

The immunoassay technology for pesticide rapid detection is based on the specific binding between pesticide antigen and antibody, so the antibody preparation is the key to the immunoassay for pesticide rapid detection. Traditional antibodies include polyclonal and monoclonal antibodies that are usually prepared by immunized animals, and the latter is widely used in pesticide immunoassay because of its strong specificity to only one antigen recognition site (epitope). However, the production of monoclonal antibodies by hybridoma cells is costly and time-consuming, and requires long-term cryopreservation and regular domestication. Even in these processes, hybridoma cells cannot produce effective antibodies due to improper preservation condition and functional gene loss or mutation during the long-term cell passage. With the development of genetic engineering technique, recombinant antibodies with clear sequences have gradually become a research hotspot, including single chain antibodies, Fab antibodies, and intact recombinant antibodies. Among the recombinant antibody expression systems, the mammalian cell expression system can guide the correct folding of recombinant antibodies and provide accurate posttranslational processing and modification functions. So it can stably produce recombinant antibodies those are consistent with the activity of parental antibodies. It not only confirms the accuracy of the parental antibody variable region sequence, but also solves many problems in conventional antibody preparation, such as the differences from various batches of traditional antibodies and the risk of cell-lines' failing to produce effective antibodies as mentioned above. Once the correct gene sequence is obtained, various forms of recombinant antibodies (including full-length IgG intact antibody, scfv, Fab fragment, etc.) can be prepared largely in vitro without sacrificing mice to prepare ascites antibodies. So, the simple operation and short preparation cycle is conducive to the large-scale production of antibodies and contributes to the development and application of sensitive and reliable immunoassays for rapid detection of pesticide residues.

SUMMARY

In order to overcome the shortcomings in the prior art, the present disclosure provides a stable production and preparation method of an intact recombinant antibody that is highly sensitive and specific to clothianidin, as well as the antibody application.

The present disclosure solves the technical problem with the following technical solution: a variable region sequence of a specific antibody against clothianidin, where a gene encoding a heavy chain variable region has an amino acid sequence shown in SEQ ID NO: 2.

Preferably, the gene encoding a heavy chain variable region may have a nucleotide sequence shown in SEQ ID NO: 1.

Preferably, the gene encoding a light chain variable region may have an amino acid sequence shown in SEQ ID NO: 4.

Preferably, the gene encoding a light chain variable region may have a nucleotide sequence shown in SEQ ID NO: 3.

The present disclosure further provides an intact recombinant antibody against clothianidin, including a heavy chain constant region, a heavy chain variable region, a light chain constant region, and a light chain variable region, where a gene encoding the heavy chain variable region has an amino acid sequence shown in SEQ ID NO: 2.

Preferably, the gene encoding the heavy chain variable region may have a nucleotide sequence shown in SEQ ID NO: 1.

Preferably, a gene encoding the light chain variable region may have an amino acid sequence shown in SEQ ID NO: 4.

Preferably, the gene encoding the light chain variable region may have a nucleotide sequence shown in SEQ ID NO: 3.

The present disclosure further provides an antibody expression plasmid, where a nucleotide sequence containing any one of above heavy chain variable regions and a mouse IgG1 heavy chain constant region can express a heavy chain protein of an intact recombinant antibody against clothianidin; alternatively, a nucleotide sequence containing the light chain variable region according to any one of claims 3 to 4 and a mouse kappa light chain constant region can express a light chain protein of an intact recombinant antibody against clothianidin.

The present disclosure further provides an immunochromatographic strip for rapid detection of clothianidin residue, containing the above-mentioned intact recombinant antibody against clothianidin.

The heavy chain and light chain variable region genes of a hybridoma cell line that can stably secrete high-specific and high-sensitive monoclonal antibodies against clothianidin were successfully amplified, sequenced and synthesized. The heavy chain and light chain expression vectors were developed by homologous recombination, and co-transfected into mammalian cells HEK293F, and finally the intact recombinant antibody against clothianidin was obtained. The recombinant antibody was verified by ELISA and surface plasmon resonance (SPR). Compared with the traditional ascitic monoclonal antibody against clothianidin, the intact recombinant antibody has consistently high-sensitivity and high-selectivity, and can replace the ascitic monoclonal antibody for the residue detection of clothianidin.

A rapid detection of clothianidin residues in environment and agricultural products was developed by using the gold-labelled test strip immunoassay based on the intact recombinant antibody, and the limit of detection (LOD) was as low as 2.5 ng/mL.

Compared with the prior art, the present disclosure has the following advantages. The heavy chain variable region and light chain variable region sequences of the intact recombinant antibody in the present disclosure are derived from a highly specific anti-clothianidin monoclonal cell line obtained by multiple immunization, cell fusion and screening. The sequence genes obtained by the present disclosure are connected to an expression vector containing a heavy chain constant region gene or a light chain constant region gene, respectively, and the intact recombinant antibody is expressed and obtained by using mammalian cells with a double-plasmid system. This ensures the recognition activity of the murine parental antibody and enables the specific antibody against clothianidin to be stably produced on a large scale, providing a reliable core-reagent for various immunoassay methods of clothianidin detection.

On the basis of preparing the anti-clothianidin intact recombinant antibody, it is applied to the rapid detection of clothianidin. The immunochromatographic test strip using the intact recombinant antibody against clothianidin has high sensitivity and high specificity.

DESCRIPTION OF THE EMBODIMENTS

To enable those skilled in the art to better understand the solutions of the present disclosure, the technical solutions in the examples of the present disclosure will be clearly and completely described below in conjunction with the accompanying drawings in the examples of the present disclosure. Obviously, the described examples are only a part of, not all of, the examples of the present disclosure. Based on the examples of the present disclosure, all other examples obtained by those of ordinary skill in the art without creative work shall fall within the protection scope of the present disclosure. Unless otherwise specified, all experimental methods in the examples are conventional.

An intact recombinant antibody against clothianidin provided by the present disclosure includes a heavy chain constant region, a heavy chain variable region, a light chain constant region, and a light chain variable region. The heavy chain constant region sequence thereof is a mouse IgG1 heavy chain constant region sequence, and the light chain constant region sequence of the antibody is a mouse kappa light chain constant region sequence.

Preparation of the Intact Recombinant Antibody Against Clothianidin

1) Gene Amplification of Variable Region of Monoclonal Antibody Against Clothianidin A hybridoma cell-line B2 prepared by mouse immunization, cell fusion and hybridoma cell screening could secrete specific antibody against clothianidin, and the subtype was IgG1/kappa. The total RNA of cell-line B2 was extracted by Trizol method and identified by agar gel electrophoresis. The integrity of RNA could meet the requirements of this experiment. RNA was used as a template to synthesize specific cDNA by reverse transcription using 5' Race technology (SMARTer RACE 5/3' Kit). Herein, upstream primers for the heavy and light chains were the adapter primers included in the kit; the specific downstream primer for the heavy chain is CTCAATTTTCTTGTCCACCTTGGT (SEQ ID NO: 5), and the specific downstream primers for the light chain are CTCATTCCTGTTGAAGCTCTTGACAATGGG (SEQ ID NO: 6) and CTCATTCCTGTTGAAGCTCTTGACGACGGG (SEQ ID NO: 7).

The PCR amplification program was:

| | |
|---|---|
| 95° C. for 45 s | |
| 68° C. for 45 s | 25 cycles |
| 72° C. for 3 min | |

Figure 1:
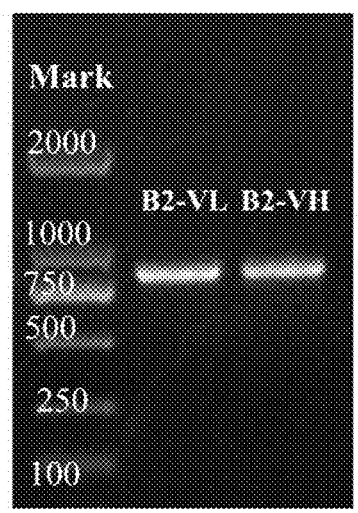
FIG. 1 illustrates the agarose gel electrophoresis results of PCR amplification of a heavy chain variable region gene and a light chain variable region gene using cDNA as a template obtained by reverse transcription based on 5'RACE technology in the present disclosure.

The agarose gel electrophoresis results of PCR amplified products are shown in FIG. 1. Bands containing VH and VL gene fragments were amplified. Purified by a gel extraction kit, purified products were cloned into a pEASY-Blunt vector, transformed, and sequenced. After sequences were aligned to the NCBI database by Blast, VH and VL genes with intact sequences, consistent subtypes, and correct expression cassettes were identified.

Monoclonal antibody B2 heavy chain variable region sequence is as follows:

(SEQ ID NO: 1)
GAGGTCCAGCTGCAGCAGTCTGGACCTGAGCTGGTGAAGCCTGGGGCTTC

AGTGAAGATGTCCTGCAAGGCTTCTGGATACACATTCACTAACTATGTTA

TGCACTGGGTGAAGCAGAAGCCTGGGCAGGGCCTTGAGTGGATTGGATTT

TTTTATCCTTACATTGATTATACTAAATACAATGAGATGTTCAAGGGCAA

GGCCACACTGACTTCAGACACATCCTCCAGCACAGCCTACATGGAACTCA

GCGGCCTGACCTCTGAGGACTCTGCGGTCTATTTCTGTGCAAGATCACAG

TTCTTCTATAGATACGACTACTTTGACTACTGGGGCCAAGGCACCGCTCT

CACAGTCTCCTCA

The functional heavy chain variable region has a full length of 363 bases. Starting from base 1, the domain encodes 121 amino acids. The functional heavy chain belongs to IGHV1-14*01, and the matching rate is 94.9% for the V region and 97.9% for the J region.

The domain is defined by IMGT method, and the specific domain is divided into the following:

| Domain | FR1 | CDR1 | FR2 | CDR2 | FR3 | CDR3 | FR4 |
|---|---|---|---|---|---|---|---|
| Base sequence | 1 to 75 | 76 to 99 | 100 to 150 | 151 to 174 | 174 to 288 | 289 to 330 | 331 to 363 |

The amino acid sequence of the monoclonal antibody B2 heavy chain variable region is as follows:

(SEQ ID NO: 2)
EVQLQQSGPELVKPGASVKMSCKASGYTFTNYVMHWVKQKPGQGLEWIGF

FYPYIDYTKYNEMFKGKATLTSDTSSSTAYMELSGLTSEDSAVYFCARSQ

FFYRYDYFDYWGQGTALTVSS

The amino acid sequence of the monoclonal antibody B2 light chain variable region is as follows:

(SEQ ID NO: 3)
GATGTTTTGATGACCCAAACTCCACTCTCCCTGCCTGTCAGTCTTGGAGA

TCAAGCCTCCATCTCTTGCAGATCCAGTCAGAACATTGTGCACAGTAATG

GAAACACCTATTTAGAATGGTACCTGCAGAAACCAGGCCAGTCTCCAAAA

GTCCTGATCTACAAAGTTTCCAACCGATTTTCTGGGGTCCCAGATAGGTT

CAGTGGCAGTGGATCAGGGACAGATTTCACACTCAAGATCAACAGAGTGG

AGGCTGAGGATCTGGGAATTTATTACTGCTTTCAAGGTTCACATGTTCCA

TTCACGTTCGGCTCGGGGACAAAGTTGGAAATAAAA

The functional light chain variable region has a full length of 336 bases. Starting from base 1, the domain encodes 112 amino acids. The functional light chain belongs to IGKV1-117*01, and the matching rate is 97.0% for the V region and 96.0% for the J region.

The domain is defined by IMGT method, and the specific domain is divided into the following:

| Domain | FR1 | CDR1 | FR2 | CDR2 | FR3 | CDR3 | FR4 |
|---|---|---|---|---|---|---|---|
| Base sequence | 1 to 78 | 79 to 111 | 112 to 162 | 163 to 171 | 172 to 279 | 280 to 306 | 307 to 336 |

The amino acid sequence of the monoclonal antibody B2 light chain variable region is as follows:

(SEQ ID NO: 4)
DVLMTQTPLSLPVSLGDQASISCRSSQNIVHSNGNTYLEWYLQKPGQSPK

VLIYKVSNRFSGVPDRFSGSGSGTDFTLKINRVEAEDLGIYYCFQGSHVP

FTFGSGTKLEIK

2) Construction of Expression Vector

After identifying the correct heavy and light chain variable region genes of antibody B2, the correct gene sequence was synthesized. The heavy and light chain variable region genes were connected to linearized expression vectors pCDNA3.4-Mouse-IgG1 and pCDNA3.4-Mouse-Kappa by homologous recombination, respectively. Herein, the pCDNA3.4-Mouse-IgG1 contained a mouse IgG1 heavy chain constant region gene, and the pCDNA3.4-Mouse-Kappa contained a mouse kappa light chain constant region gene. Therefore, the constructed heavy or light chain recombinant plasmids contain heavy chain variable region gene and constant region gene or light chain variable region gene and constant region gene, respectively. The heavy or light chain expression vector was transformed into Ti competent cells, cultured under shaking, and then sequenced.

3) Expression of the Intact Recombinant Antibody

Figure 2:
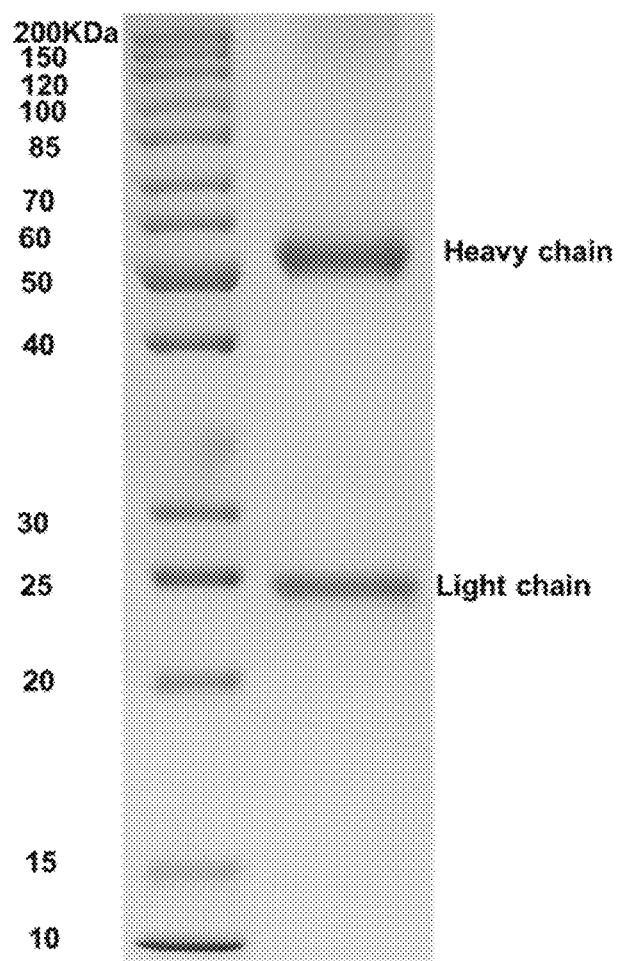
FIG. 2 illustrates the verification of the expression of the intact recombinant antibody against clothianidin in a mammalian cell HEK293F by sodium dodecyl sulfate-polyacrylamide gel electrophoresis (SDS-PAGE) in the present disclosure.

The bacterial suspension corresponding to the correctly sequenced plasmid was cultured and amplified in a large volume, followed by extracting the plasmid for later use. HEK293F cells were resuscitated and cultured in suspension at 120 rpm, 8% $CO_2$, and 37° C. for 3 generations. Before transfection, the cells were seeded into a new culture flask with a seeding density of $1.5\times10^6$ cells/mL. After suspension culture for 2 h, the heavy-chain plasmid, light-chain plasmid and transfection reagent were mixed well into a certain ratio and incubate for 15 min and then transfected into HEK293F cells. The transfected cells were cultured in suspension until the survival rate was less than 70%. After centrifugation at 4000 rpm for 5 min, the supernatant was collected. The intact recombinant antibody in the cell supernatant was purified by Protein A affinity chromatography, and the liquid flow rate during the purification was 1 mL/min. The purified antibody was dialyzed overnight with 0.01 M PBS solution. After dialysis, the antibody concentration was determined to be 3 mg/mL, which was verified by SDS-PAGE (FIG. 2).

Characterization of the Intact Recombinant Antibody

Figure 3:
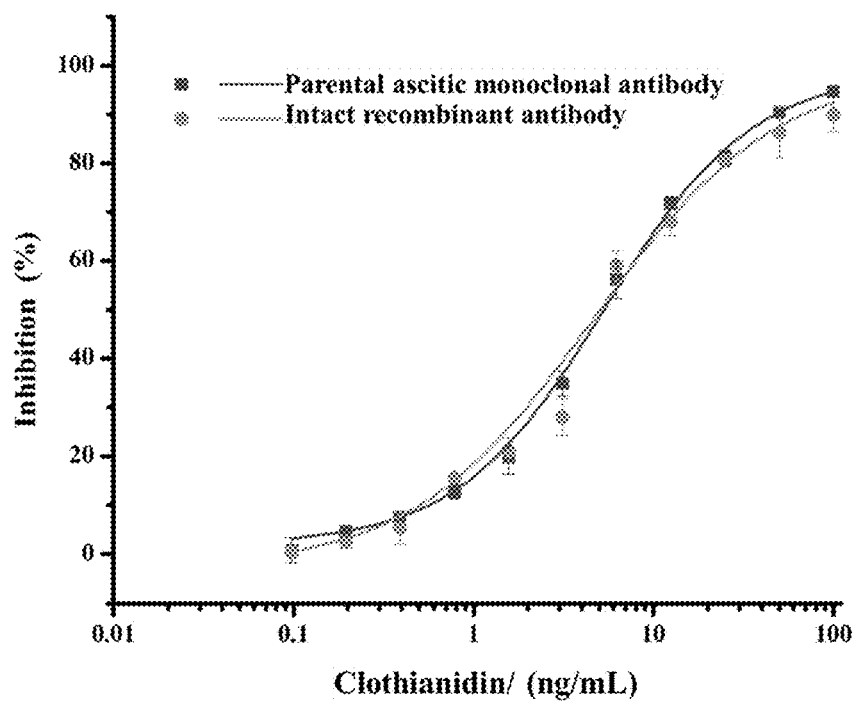
FIG. 3 illustrates ELISA competition curves of an intact recombinant antibody against clothianidin (pesticide concentrations, from low to high, are 0.01, 0.20, 0.39, 0.78, 1.56, 3.13, 6.25, 12.5, 25, 50, and 100 ng/mL).

1) Comparison of Anti-Clothianidin Intact Recombinant Antibody and Anti-Clothianidin Natural Mouse Ascitic Monoclonal Antibody by ELISA In the early preparation stage of parental ascitic monoclonal antibodies, the assay sensitivity difference was compared between the homologous competitive indirect ELISA (coating antigen was clothianidin-OVA) and the heterologous competitive indirect ELISA (coating antigen was imidaclothiz-OVA). It was found that the sensitivity of the ELISA method was higher when imidaclothiz-OVA was used as a heterologous coating antigen. Therefore, in the present disclosure, the heterologous competitive indirect ELISA was used to evaluate the sensitivity and specificity of the intact recombinant antibody against clothianidin. A 96-well plate was coated with imidaclothiz-OVA as the heterologous competitive antigen; subsequently, ELISA was performed using a rabbit anti-mouse IgG-HRP as a detection antibody, tetramethylbenzidine (TMB) as a reaction substrate, and clothianidin and other neonicotinoid pesticide standards as analytes. The results (FIG. 3) are as follows:

a) Detection Range

The detection range of the intact recombinant antibody against clothianidin for ELISA ($IC_{20}$-$IC_{80}$) was 0.92-23.04 ng/mL.

The detection range of the ascitic monoclonal antibody against clothianidin for ELISA ($IC_{20}$-$IC_{80}$) was 1.45-20.01 ng/mL.

b) Sensitivity ($IC_{50}$)

The $IC_{50}$ of the intact recombinant antibody against clothianidin was 4.62 ng/mL.

The $IC_{50}$ of the ascitic monoclonal antibody against clothianidin was 5.39 ng/mL.

c) Specificity by ELISA

In the present disclosure, the specificity of the antibody was evaluated by detecting the cross-reactivity with seven common neonicotinoid insecticides. The data of ELISA showed that the intact recombinant antibody and mouse monoclonal antibody prepared in the present disclosure had no cross-reactivity with other seven common neonicotinoid insecticides (cross-reactivity<0.1%), and could be used for specific analysis of clothianidin. The results also showed that the intact recombinant antibody had highly consistent selectivity with the parental monoclonal antibody.

2) Characterization of Antibody Binding Kinetics by Surface Plasmon Resonance (SPR)

The CM7 chip was used in this invention, and the optimal pH for both antibodies was 5.0. The final signal values of the antibodies coupled on the chip were 38663 RU and 39854 RU, respectively. Kinetic experiments were performed to determine the affinity of both the parental ascitic monoclonal antibody and the intact recombinant antibody to clothianidin at a range of analyte concentrations (50, 25, 12.5, 6.25, 3.12, 1.623, and 0.78 nM). The KD were $5.05\times10^{-9}$ M and $3.24\times10^{-9}$ M, respectively, indicating that the affinity of the intact recombinant antibody to clothianidin was very close to that of the ascitic antibody.

Example 3: Application of the Intact Recombinant Antibody on Gold Test Strips

As verified by ELISA and SPR method, the intact recombinant antibody against clothianidin prepared by this method can replace the ascitic antibody. In order to achieve the rapid detection of clothianidin, this invention prepares a competitive immunochromatographic test strip for clothianidin detection.

1) Preparation of Gold-Labelled Antibody

The optimal buffer for labeling in this method was determined to be 0.01 M PBS, the optimal pH was 6.5, and the optimal amount of labelled antibody was 75 μg/mL. An appropriate amount of antibody was added into 10 mL of colloidal gold solution and mixed well. After incubation at room temperature for 1 h, the gold-labelled antibody solution was blocked by 10% BSA and 1% PEG 20000 (the final concentrations were 1% and 0.1%, respectively), and then incubated at room temperature for 1 h. After centrifuging at 13500 g, 4° C. for 30 min, the collected sediment was redissolved with the buffer containing 1% BSA and 0.1% PEG20000 pH6.5, and centrifuged again to remove the unbound antibody. Then, the sediment was resuspended with 1 mL of the buffer (containing 5% sucrose and 1% BSA) for later use.

2) Assembly of Test Strips

Immunochromatographic test strips were made of plastic liner, absorbent pad, NC membrane, sample pad (pre-treated with 1% BSA, 0.1% PEG20000, 0.25% PVP), gold-labelled conjugate pad, test line (0.15 mg/mL of imidaclothiz-OVA) and control line (0.09 mg/mL of goat anti-mouse IgG), assembled according to the conventional test strip assembly method.

3) Sensitivity Experiment of Test Strip

Figure 4:
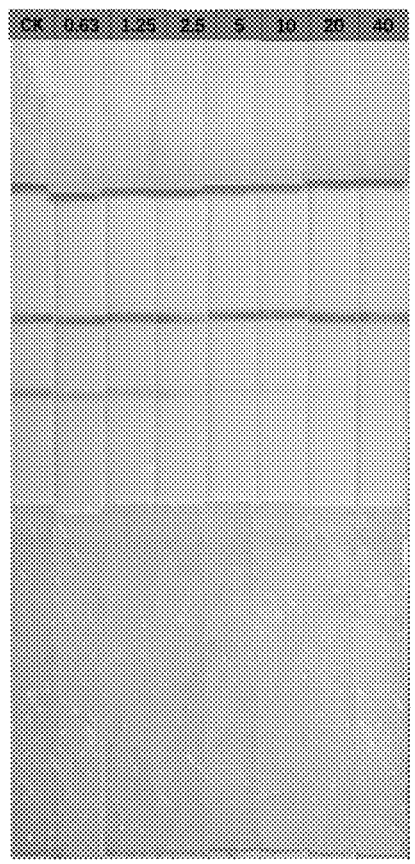
FIG. 4 illustrates detection of clothianidin standard solutions by gold test strip based on the intact recombinant antibody (pesticide concentrations, from low to high, are CK (blank control), 0.63, 1.25, 2.5, 5, 10, 20, 40 ng/mL).

Clothianidin stock solution of 100 μg/mL was prepared with pure methanol, and a series of standard working solutions at 0.63, 1.25, 2.5, 5, 10, 20, and 40 ng/mL were prepared with 0.01M PBS buffer to test the same batch of strips. The test results are shown in FIG. 4. Judging by naked eyes, when the concentration of clothianidin was above 2.5 ng/mL, the color of T line was obviously weakened. When the concentration of clothianidin was above 10 ng/mL, the T line disappeared. And other seven neonicotinoid pesticide solutions were used to test the specificity of the test strip. The standard solution was diluted with 0.01M PBS to 1000 ng/mL for testing. After 15 minutes, compared the color of the test strip T line with the results of clothianidin, and the specificity of the method could be determined according to the color of the T line. The results showed that compared with the color of T line from the sample CK (blank control)

without any pesticide, the color of T lines from the seven structural analogs of clothianidin was not significantly weakened, so the results were negative.

In short, the gold test strips based on the recombinant antibody against clothianidin in the present disclosure has strong specificity and high sensitivity. The visual LOD of clothianidin is 2.5 ng/mL, which can be used for rapid detection of clothianidin residues in environment and agricultural products.

The above method is used to explain the invention, not to limit. Any modifications and changes made to the invention within the spirit of the invention and the protection scope of the claims fall within the protection range of the invention.

What is claimed is:

1. An intact recombinant antibody against clothianidin, comprising a heavy chain constant region, a heavy chain variable region, a light chain constant region, and a light chain variable region, wherein the amino acid sequence of the heavy chain variable region comprises SEQ ID NO: 2, and the amino acid sequence of the light chain variable region comprises SEQ ID NO: 4.

2. The intact recombinant antibody against clothianidin according to claim 1, wherein a gene encoding the heavy chain variable region comprises the nucleotide sequence of SEQ ID NO: 1.

3. The intact recombinant antibody against clothianidin according to claim 1, wherein a gene encoding the light chain variable region comprises the nucleotide sequence of SEQ ID NO: 3.

4. An expression plasmid for expressing an intact recombinant antibody against clothianidin, comprising:
- the heavy chain variable region nucleotide sequence of SEQ ID NO: 1;
- a nucleotide sequence of a mouse IgG1 heavy chain constant region;
- the light chain variable region nucleotide sequence of SEQ ID NO: 3; and
- a nucleotide sequence of a mouse kappa light chain constant region.

5. An immunostrip for rapid detection of clothianidin residue, comprising the intact recombinant antibody against clothianidin according to claim 1.

6. An immunostrip for rapid detection of clothianidin residue, comprising the intact recombinant antibody against clothianidin according to claim 2.

7. An immunostrip for rapid detection of clothianidin residue, comprising the intact recombinant antibody against clothianidin according to claim 3.

* * * * *

SEQUENCE LISTING

<160> NUMBER OF SEQ ID NOS: 7

<210> SEQ ID NO 1
<211> LENGTH: 363
<212> TYPE: DNA
<213> ORGANISM: Mus musculus

<400> SEQUENCE: 1

```
gaggtccagc tgcagcagtc tggacctgag ctggtgaagc ctggggcttc agtgaagatg      60
tcctgcaagg cttctggata cacattcact aactatgtta tgcactgggt gaagcagaag     120
cctgggcagg gccttgagtg gattggattt ttttatcctt acattgatta tactaaatac     180
aatgagatgt tcaagggcaa ggccacactg acttcagaca tcctccag cacagcctac       240 atggaactca gcggcctgac ctctgaggac tctgcggtct atttctgtgc aagatcacag     300
ttcttctata gatacgacta ctttgactac tggggccaag gcaccgctct cacagtctcc     360
tca                                                                   363
```

<210> SEQ ID NO 2
<211> LENGTH: 121
<212> TYPE: PRT
<213> ORGANISM: Mus musculus

<400> SEQUENCE: 2

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asn Tyr
            20                  25                  30

Val Met His Trp Val Lys Gln Lys Pro Gly Gln Gly Leu Glu Trp Ile
        35                  40                  45

Gly Phe Phe Tyr Pro Tyr Ile Asp Tyr Thr Lys Tyr Asn Glu Met Phe
    50                  55                  60

Lys Gly Lys Ala Thr Leu Thr Ser Asp Thr Ser Ser Thr Ala Tyr
65                  70                  75                  80

Met Glu Leu Ser Gly Leu Thr Ser Glu Asp Ser Ala Val Tyr Phe Cys
                85                  90                  95

Ala Arg Ser Gln Phe Phe Tyr Arg Tyr Asp Tyr Phe Asp Tyr Trp Gly
            100                 105                 110

Gln Gly Thr Ala Leu Thr Val Ser Ser
        115                 120
```

<210> SEQ ID NO 3
<211> LENGTH: 336
<212> TYPE: DNA
<213> ORGANISM: Mus musculus

<400> SEQUENCE: 3

```
gatgttttga tgacccaaac tccactctcc ctgcctgtca gtcttggaga tcaagcctcc      60
atctcttgca gatccagtca gaacattgtg cacagtaatg gaaacaccta tttagaatgg     120
```

```
tacctgcaga aaccaggcca gtctccaaaa gtcctgatct acaaagtttc caaccgattt    180
tctggggtcc cagataggtt cagtggcagt ggatcaggga cagatttcac actcaagatc    240
aacagagtgg aggctgagga tctgggaatt tattactgct ttcaaggttc acatgttcca    300
ttcacgttcg gctcggggac aaagttggaa ataaaa                              336

<210> SEQ ID NO 4
<211> LENGTH: 112
<212> TYPE: PRT
<213> ORGANISM: Mus musculus

<400> SEQUENCE: 4

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Asn Ile Val His Ser
            20                  25                  30

Asn Gly Asn Thr Tyr Leu Glu Trp Tyr Leu Gln Lys Pro Gly Gln Ser
        35                  40                  45

Pro Lys Val Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Asn Arg Val Glu Ala Glu Asp Leu Gly Ile Tyr Tyr Cys Phe Gln Gly
                85                  90                  95

Ser His Val Pro Phe Thr Phe Gly Ser Gly Thr Lys Leu Glu Ile Lys
            100                 105                 110

<210> SEQ ID NO 5
<211> LENGTH: 24
<212> TYPE: DNA
<213> ORGANISM: Artificial Sequence
<220> FEATURE:
<223> OTHER INFORMATION: Synthesized downstream primer for heavy chain

<400> SEQUENCE: 5
ctcaattttc ttgtccacct tggt                                            24

<210> SEQ ID NO 6
<211> LENGTH: 30
<212> TYPE: DNA
<213> ORGANISM: Artificial Sequence
<220> FEATURE:
<223> OTHER INFORMATION: Synthesized downstream primer for light chain

<400> SEQUENCE: 6
ctcattcctg ttgaagctct tgacaatggg                                      30

<210> SEQ ID NO 7
<211> LENGTH: 30
<212> TYPE: DNA
<213> ORGANISM: Artificial Sequence
<220> FEATURE:
<223> OTHER INFORMATION: Synthesized downstream primer for light chain

<400> SEQUENCE: 7
ctcattcctg ttgaagctct tgacgacggg                                      30
```